(12) United States Patent
Kim et al.

(10) Patent No.: US 12,147,214 B2
(45) Date of Patent: Nov. 19, 2024

(54) COMPUTER AIDED DESIGN MATRIX FOR THE MANUFACTURE OF DENTAL DEVICES

(71) Applicant: PROSOMNUS SLEEP TECHNOLOGIES, INC., Pleasanton, CA (US)

(72) Inventors: Sung Kim, Pleasanton, CA (US); David W. Kuhns, Pleasanton, CA (US); Leonard A. Liptak, Pleasanton, CA (US)

(73) Assignee: PROSOMNUS SLEEP TECHNOLOGIES, INC., Pleasonton (CA)

( * ) Notice: Subject to any disclaimer, the term of this patent is extended or adjusted under 35 U.S.C. 154(b) by 23 days.

(21) Appl. No.: 17/443,613

(22) Filed: Jul. 27, 2021

(65) Prior Publication Data
US 2022/0019192 A1   Jan. 20, 2022

Related U.S. Application Data

(63) Continuation of application No. 15/991,991, filed on May 29, 2018, now abandoned, which is a
(Continued)

(51) Int. Cl.
*A61C 13/00* (2006.01)
*A61C 5/00* (2017.01)
(Continued)

(52) U.S. Cl.
CPC .......... *G05B 19/4097* (2013.01); *A61C 5/007* (2013.01); *A61C 7/002* (2013.01);
(Continued)

(58) Field of Classification Search
CPC ................................ A61C 5/007; A61C 13/00
See application file for complete search history.

(56) References Cited

U.S. PATENT DOCUMENTS 9,808,327 B1 * 11/2017 Kim .................... A61B 1/24
9,949,868 B2 * 4/2018 Kim .................... A61C 7/36
(Continued)

FOREIGN PATENT DOCUMENTS

WO   WO-2015103084 A1 *  7/2015  .............. A61C 7/08

*Primary Examiner* — Andrew D Graham
(74) *Attorney, Agent, or Firm* — Procopio, Cory, Hargreaves & Savitch LLP

(57) ABSTRACT

Disclosed herein are methods of manufacturing a dental device, the method comprising: obtaining a set of clinical options for the dental device from a health care provider; creating a first data set from the set of clinical options; communicating the data set to a computer aided design (CAD) software; preparing a digital design for the dental device using the CAD software; communicating the digital design to an automated milling apparatus; and automatedly milling a block of polymer to obtain the dental device. Also disclosed are dental devices manufactured by the above method. Further disclosed are methods of treating or ameliorating apnea jaw-related disorder in a patient, the method comprising obtaining a dental device manufactured by the above method and positioning the dental device over the dentition prior to sleep, whereby the mandible is advanced forward relative to the maxilla, thereby ameliorating the symptoms of sleep apnea or the jaw-related disorder.

22 Claims, 7 Drawing Sheets

Related U.S. Application Data continuation of application No. 15/651,874, filed on Jul. 17, 2017, now abandoned.

(60) Provisional application No. 62/365,970, filed on Jul. 22, 2016.

(51) Int. Cl.
    *A61C 7/00*    (2006.01)
    *A61C 7/08*    (2006.01)
    *A61F 5/56*    (2006.01)
    *G05B 19/4097*    (2006.01)

(52) U.S. Cl.
    CPC ............ *A61C 7/08* (2013.01); *A61C 13/0004* (2013.01); *A61F 5/566* (2013.01); *A61F 2005/563* (2013.01); *G05B 2219/35012* (2013.01); *G05B 2219/45145* (2013.01)

(56) References Cited

U.S. PATENT DOCUMENTS

| | | | |
|---|---|---|---|
| 2004/0197727 A1* | 10/2004 | Sachdeva | A61C 7/00 433/24 |
| 2008/0228303 A1* | 9/2008 | Schmitt | A61C 13/0004 700/98 |
| 2009/0316966 A1* | 12/2009 | Marshall | G06T 19/00 382/128 |
| 2010/0043805 A1* | 2/2010 | Kelly | A61F 5/566 433/213 |
| 2011/0059413 A1* | 3/2011 | Schutyser | A61B 6/14 433/214 |
| 2011/0155144 A1* | 6/2011 | Tousssaint | A61F 5/566 29/527.1 |
| 2012/0015316 A1* | 1/2012 | Sachdeva | G16H 40/20 382/128 |
| 2012/0115107 A1* | 5/2012 | Adams | A61B 5/4542 433/215 |
| 2012/0199136 A1* | 8/2012 | Urbano | A61F 5/566 128/848 |
| 2012/0214121 A1* | 8/2012 | Greenberg | A61B 6/14 433/213 |
| 2013/0284184 A1* | 10/2013 | Wagner | A61C 7/006 128/848 |
| 2013/0295516 A1* | 11/2013 | Singer | A61C 7/36 433/19 |
| 2013/0298917 A1* | 11/2013 | Poisson | A63B 71/085 128/861 |
| 2014/0076333 A1* | 3/2014 | Ona | A61F 5/566 264/16 |
| 2014/0080083 A1* | 3/2014 | Mathieu | A61C 7/08 128/848 |
| 2014/0107408 A1* | 4/2014 | Rostami | A61F 5/01 600/37 |
| 2014/0238414 A1* | 8/2014 | Lucas | A61C 7/08 128/861 |
| 2014/0238415 A1* | 8/2014 | Lucas | A61C 7/08 128/861 |
| 2014/0326253 A1* | 11/2014 | Baratier | A61F 5/566 382/128 |
| 2014/0329194 A1* | 11/2014 | Sachdeva | A61C 7/002 433/24 |
| 2014/0332011 A1* | 11/2014 | Turek | A61F 5/566 128/848 |
| 2014/0370465 A1* | 12/2014 | Lucas | A61C 5/007 433/214 |
| 2014/0379356 A1* | 12/2014 | Sachdeva | A61C 7/002 705/2 |
| 2015/0079531 A1* | 3/2015 | Heine | A61C 7/08 433/19 |
| 2015/0157491 A1* | 6/2015 | Hofmann | A61F 5/566 128/848 |
| 2015/0238345 A1* | 8/2015 | Decker | A61C 5/007 382/128 |
| 2015/0245890 A1* | 9/2015 | Wouters | A61C 9/004 700/98 |
| 2016/0074207 A1* | 3/2016 | Choi | A61F 5/566 128/848 |
| 2016/0184129 A1* | 6/2016 | Liptak | A61C 7/08 128/848 |
| 2016/0199157 A1* | 7/2016 | Boronkay | A61F 5/56 128/848 |
| 2016/0374784 A1* | 12/2016 | Joshi | A61C 9/0053 433/214 |
| 2017/0143537 A1* | 5/2017 | Kim | A61C 7/08 |
| 2018/0078344 A1* | 3/2018 | Falkel | A61C 7/36 |
| 2019/0033826 A1* | 1/2019 | Kim | G05B 19/4097 |

\* cited by examiner

COMPUTER AIDED DESIGN MATRIX FOR THE MANUFACTURE OF DENTAL DEVICES

RELATED APPLICATIONS

The present application is a continuation of U.S. patent application Ser. No. 15/991,991, filed May 29, 2018, which is a continuation of U.S. patent application Ser. No. 15/651,874 filed Jul. 17, 2017, by KIM et al., and entitled "A COMPUTER AIDED DESIGN MATRIX FOR THE MANUFACTURE OF ORAL APPLIANCES," which in turn claims priority to the U.S. Provisional Application Ser. No. 62/365,970 filed Jul. 22, 2016, by LIPTAK et al., and entitled "A COMPUTER AIDED DESIGN MATRIX FOR THE MANUFACTURE OF ORAL APPLIANCES," the entire disclosure of both of which, including any drawings, is incorporated by reference herein.

FIELD OF THE INVENTION

The present invention is in the field of dental devices. In particular, the present invention is in the field of a computer aided design procedure for preparing a design and manufacturing a dental device.

BACKGROUND OF THE DISCLOSURE

The use of dental devices to treat sleep apnea is well-known in the art. These devices use several different techniques for moving the mandible forward when the device is worn, in order to open the patient's airway, particularly during the sleep hours, and thereby reduce the occurrence of sleep apnea. In addition, health care providers, patients, and manufacturers have a wide variety of options in choosing the style of the device, the material with which the device is made, and accessories used with the device. These options are generally determined by the patient anatomy, patient comfort, health care provider bias, and the manufacturing ease.

Currently, dental devices are hand-crafted artisanally to the health care provider's specification. Each laboratory or medical device manufacturer is capable of manufacturing one type, or at most, a select few of the options. If different styles of mandibular advancement devices, or combination of mandibular advancement devices with other splints utilizing the same patient data, are desired then the patient or the health care provider must contact multiple laboratories. Accordingly, currently it is economically impossible to prepare multiple sets of devices for a patient. As the result, in many cases the patient is not receiving the device that is the best fit for their needs.

SUMMARY OF THE INVENTION

Disclosed herein are methods of manufacturing dental devices, the method comprising: obtaining a set of clinical options for the dental devices from a health care provider in the form of a prescription herein referred to as the "Rx," which includes the treatment plan for the patient; creating a first data set from the set of clinical options; communicating the data set to a computer aided design (CAD) software; preparing a digital design for the dental devices using the CAD software; communicating the digital design to an automated milling apparatus; and automatedly milling a block of polymer to obtain the dental device. Also disclosed are dental devices manufactured by the above method. Further disclosed are methods of treating or ameliorating sleep apnea or a jaw-related disorder in a patient, the method comprising obtaining a dental device manufactured by the above method and positioning the dental device over the dentition prior to sleep, whereby the mandible is advanced forward, vertically, laterally or a combination of the three, relative to the maxilla, thereby ameliorating the symptoms of sleep apnea or the jaw-related disorder.

BRIEF DESCRIPTION OF THE DRAWINGS

FIG. 1A illustrates a front view of an embodiment of the disclosed mandibular advancement device as it is worn in the mouth, whereas

FIG. 8A shows a free standing upper splint with the retention arms, while

DETAILED DESCRIPTION OF THE EMBODIMENTS

Figure 1A:
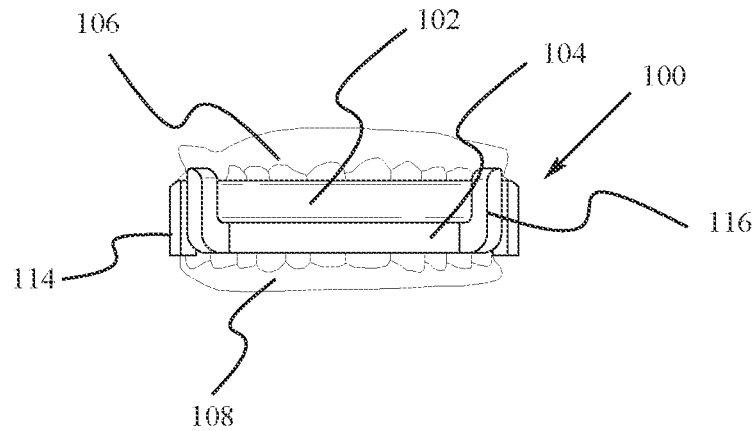

The present disclosure is directed to a method of obtaining information about a patient's dentition and the preferences of the patient and/or a health care provider in order to manufacture a set of dental appliances that match the patient's needs. Previously, embodiments of a particular dental appliance, namely a mandibular advancement device, have been disclosed. See, for example, the International Publication WO 2015/103084 (the entirety of this publication, including all the drawings, is incorporated herein by reference, in particular the following sections describing the device and the methodology of titration: Paragraphs [0019]-[0053] and FIGS. 1A-4E and 7-9). The methods and products disclosed herein are used in connection with the device described in the above-incorporated document, or any other device that is currently on the market, or other novel combinations of devices and accessories. In alternative embodiments, provided are methods of manufacturing a kit, the kit comprising a set of mandibular advancement devices, the method comprising:

a. preparing a three-dimensional electronic model of the patient's dentition;
b. converting the electronic model to a data set
c. obtaining a set of clinical options, i.e., a prescription, from a health care provider (HCP) for the treatment of the patient.
d. incorporating within a computer-aided design (CAD) software the data set and the set of clinical options;
e. automatedly manufacturing a dental appliance, having the set of clinical options, in accordance with the appliance data set;

wherein:
the set of mandibular advancement devices comprise at least one upper and at least one lower splint;
each upper and each lower splint independently comprises a fin, or a post for a fin to attach thereto:
each upper fin or post is located at a distance UD from the back of the upper splint, and each lower fin or post is located at a distance LD from the back of the lower splint;
the distances UD and LD are independently unchangeable.

In one embodiment the device creates an offset between the upper and lower splint by using upper and lower fins as boundary surfaces to restrict movement while the mouth is closed or reasonably opened.

In some embodiments, the devices disclosed herein were digitally designed and then milled as a single unit. In some of these embodiments, a computer aided design (CAD) process were used to design and manufacture the mandibular advancement devices disclosed herein. A plaster model of the patient's dental impression was first obtained using well-known techniques in the art. Then, scans of the plaster models were imported into the CAD software. In other embodiments, the 3D files of the patient's impression are imported from other sources, such as a direct scan of the patient dentition using an Intra Oral Scan (IOS) Device, e.g., the 3M TruDef™ scanner, or a direct scan of the impression from either an IOS or Cone Beam Computed Tomography (CBCT) device. In these embodiments, the files enable the design of the mandibular advancement splint in 3D space in a CAD software such as 3-Matic by Materialise™.

In other embodiments, the different components of the disclosed devices, for example the splint, the fins, the retention arms, etc., are milled or manufactured separately and then attached together after the manufacturing. This approach allows for the use of interchangeable parts.

In one embodiment the digitally designed and milled splints are reproduced accurately without manual polymer buildup. In some embodiments, accurate reproduction results in accurate replacement devices. In other embodiments, it results in reproducible titration settings. In some embodiments the splints are digitally designed and milled to provide access to pre-cured polymeric materials, and wherein the device has minimal residual monomers.

In one embodiment one or more identifying information, e.g., the patient's name, order number, and other relevant tracking information, are designed into the device. The identifying information appears on the device through the milling process.

In one embodiment, the device is designed to comfortably fit on to a patient's upper and lower arches, maintain a maximum amount of space for the tongue, and keep the mandible advanced forward per a doctor's prescription while still allowing the patient to reasonably open their mouth and move their jaw from left to right for comfort. This contact serves as a barrier to keep the lower fin in a position forward of this fin engagement surface.

The disclosed devices can be made from any material that can withstand the oral environment for an extended period of time, for example overnight. Furthermore, the material can be any material that is capable of being milled to form the devices disclosed herein. Examples of materials include plastics and other polymers, whether hard or soft, transparent or opaque. Some suitable polymers include, but are not limited to, a polyetheretherketone (PEEK), polystyrene, polyvinyl chloride, rubber, synthetic rubber, or an acrylate polymer, such as a polymer made up of methyl methacrylate, methyl acrylate, ethyl acrylate, 2-chloroethyl vinyl ether, 2-ethylhexyl acrylate, hydroxyethyl methacrylate, butyl acrylate, butyl methacrylate, or trimethylolpropane triacrylate (TMPTA).

Embodiments of the device are further described with reference to the accompanying drawings.

Figure 1B:
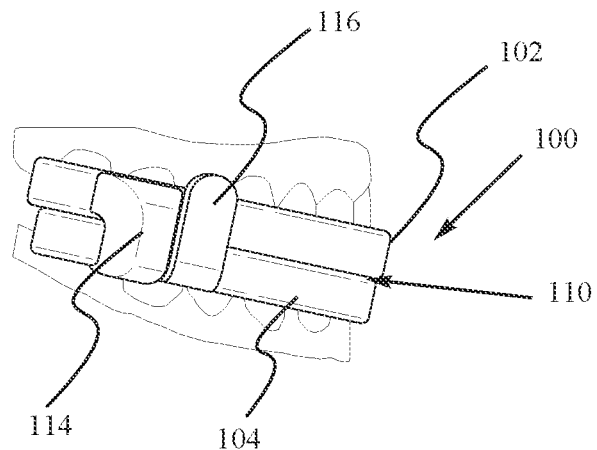
FIG. 1B shows a side view of the same embodiment.

FIG. 1 illustrates an embodiment of the disclosed mandibular advancement device, 100. FIG. 1a shows a front view of the device as it is worn in the mouth, whereas FIG. 1b shows a side view of the same embodiment. The device 100 comprises and upper splint 102 and a lower splint 104. The splint 102 is configured to fit snuggly onto the upper dentition 106, while the lower splint 104 is configured to fit snuggly onto the lower dentition 108. Each splint provides enough retention to keep the device on during normal wear but allowing the user to pull off the device with minimal effort. The two splints contact each other along the occlusal plane 110, i.e., the plane passing through the biting surfaces of the teeth.

In one embodiment the thickness of the upper splint 102 and lower splint 104 is independently varied to create a fixed amount of jaw opening between the patient's arches.

The devices 100 disclosed herein are prepared individually and specially for a particular patient. For this reason, while preparing the digital design of the disclosed devices, the idiosyncrasies of the patient's oral and dentition structures are taken into account. For instance, in some embodiments, the opposing surfaces of the splint are designed in variance with each other to accommodate the patient's oral structure to achieve maximum comfort. The surfaces can be flat or be made to touch at one or more points. This is true of any other feature of the devices 100. For example, the height, width and shape of the fins; the rake angle; the offset position of the fins; the location of retention arms, if any; the dental impressions; inter alia, are designed specifically for the particular patient. This feature is easily enabled with a device that is digitally pre-designed. The currently available devices are handmade, making it difficult for the artisan to accurately take into account the specific oral features of a particular patient.

Each upper splint 102 comprises at least one upper fin 114, and preferably two upper fins 114. The fin 114 is located to the side of the upper splint 102 such that when the splint 102 is worn by the patient, the fin 114 is near the molars. Each upper fin 114 protrudes downwardly.

Similarly, each lower splint 104 comprises at least one lower fin 116, and preferably two lower fins 116. The fin 116 is located to the side of the lower splint 104 such that when the splint 104 is worn by the patient, the fin 116 is near the molars. Each lower fin 116 protrudes upwardly.

Throughout the present disclosure, the terms "up," "upper," or "upward," and "down," "lower," or "downward" refer to the relative position of the upper jaw and the lower jaw. Thus, "protruding downwardly" means protruding away from the upper jaw and towards the lower jaw. Similarly, the words "front" or "forward" and "back" or "backward" refer to the relative position of components in the mouth. Thus, "front" means towards the lips, whereas "back" means towards the throat, when the device is in the mouth.

Figure 2A:
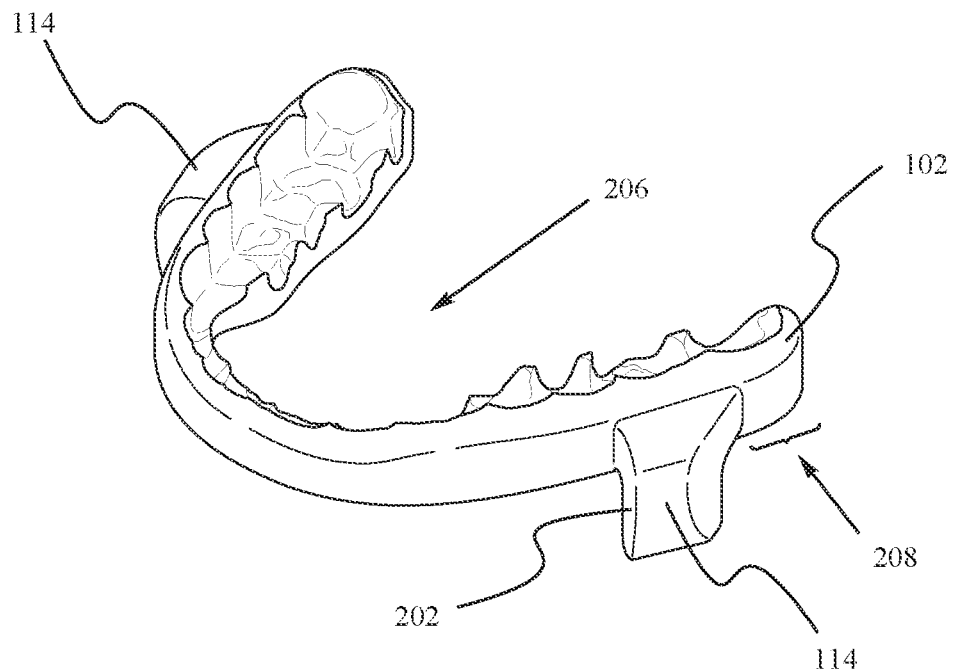
FIG. 2A illustrates an embodiment of the upper splint of the disclosed mandibular advancement devices where the rake angle is set in a neutral orientation.
Figure 2B:
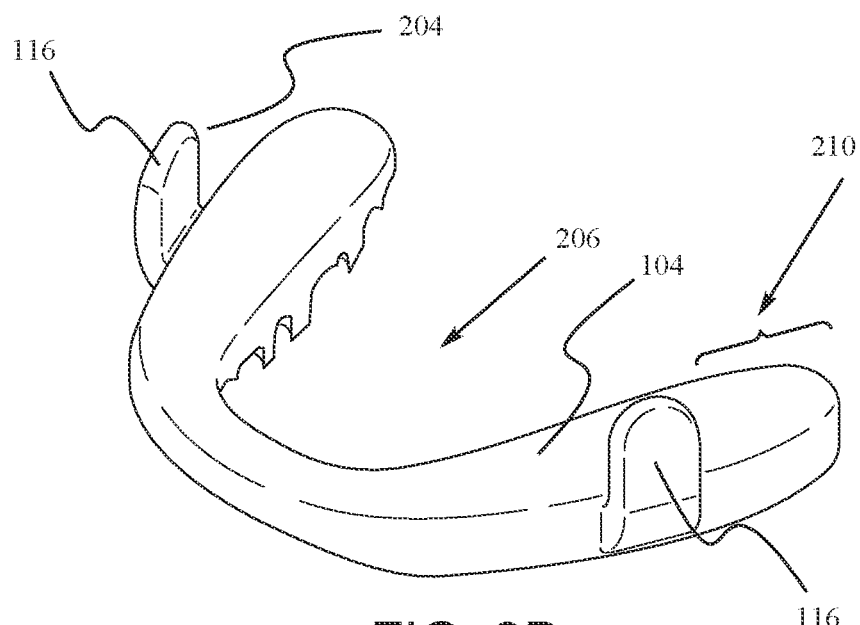
FIG. 2B is an illustration of an embodiment of the lower splint.
Figure 3A:
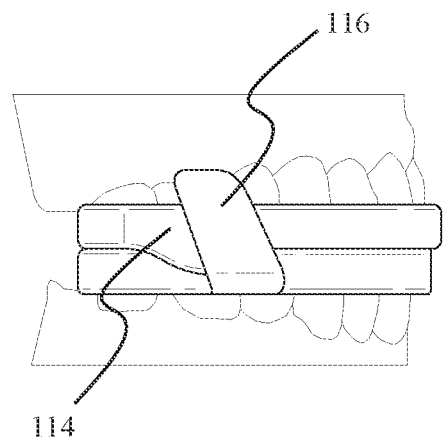
FIG. 3A illustrates an embodiment of the disclosed mandibular advancement device where the rake angle is set in a recline orientation.
Figure 3B:
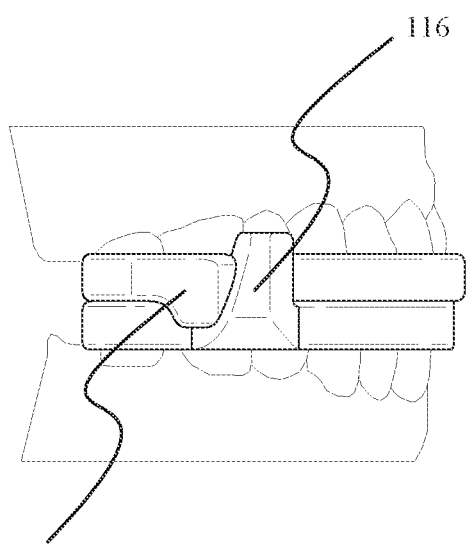
FIG. 3B illustrates an embodiment of the disclosed mandibular advancement device where the rake angle is set in a procline orientation.

FIG. 2A shows the embodiment of the upper splint that is shown in FIG. 1 and FIG. 2B shows the embodiment of the lower splint that is shown in FIG. 1. FIG. 2 depicts the splints by themselves and without being worn on the teeth.

The upper fin 114 comprises a front surface 202 and the lower fin 116 comprises a back surface 204. When the device is worn in the mouth, the lower fin 116 is located in front of the upper fin 114. The front surface 202 of the upper fin 114 contacts the back surface 204 of the lower fin 116. This contact serves as a barrier to keep the lower fin in a position forward of this fin engagement surface. That is, the contact prevents the lower jaw from moving backward relative to the upper jaw. Thus, once the device is worn, the relative forward position of the upper and lower jaws becomes fixed. The patient would be able to open and close their mouth and move the lower jaw from left to right for comfort. However, the patient would not be able to move the lower jaw backwards beyond the point of contact of the two surfaces 202,204.

In one embodiment the device is digitally designed and milled to provide optimal strength with reduced interference to the tongue creating a comfortable and durable device. As seen in FIGS. 2A & 2B, the two splints each form an arch with an empty center 206. The empty center 206 provides room for the patient's tongue when the device is in use. The type of design that allows room for the tongue is referred to as lingual-less. Thus, some embodiments of the present device 100 are lingual-less designs.

The upper fin 114 is located at a distance UD (208) from the back of the upper splint 102. Similarly, the lower fin 116 is located at a distance LD (210) from the back of the lower splint 104. Distances 208,210 are also referred to as fin offset. The relative positioning of the fins determines the degree to which the lower jaw is protruded forward, i.e., the jaw offset. As discussed below, in some embodiments, the distances 208 and 210 are manipulated to provide the best fit for the patient.

In one embodiment, the upper and lower fins vary in angular shape at the contact surfaces of each fin to provide the most anatomically correct position and comfort during the motion of opening and closing the mouth. The embodiment shown in FIG. 1 comprises vertical contact surfaces. In these embodiments, the contact surfaces 202 and 204 are perpendicular to the occlusal plain 110. In this embodiment, the rake angle, i.e., the angle that surface 202 makes with the occlusal plane 110, is 90° to the occlusal plane, i.e., a neutral angle. In other embodiments, for example those shown in FIGS. 3A and 3B, the contact surfaces are at a non-neutral angle. For example, in the embodiment shown in FIG. 3A, the rake angle is set in a recline orientation. In this embodiment, the surface 202 angles backward. Conversely, in the embodiment shown in FIG. 3B, the rake angle is set in a procline orientation. In this embodiment, the surface 202 angles forward. The rake angle is configured to drive a directional movement during the opening and closing of the mouth. The particular angle, i.e., whether neutral, incline, or procline, and the angle degree, are chosen based on clinician prescription and patient comfort.

Figures 4A, 4B, 4C, 4D:
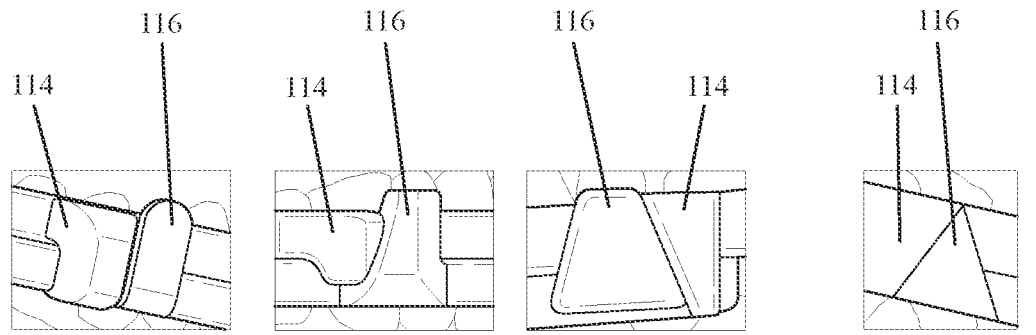
FIG. 4A illustrates an embodiment of the fin design in a predesigned digital library of fins.
FIG. 4B illustrates another embodiment of the fin design in a predesigned digital library of fins.
FIG. 4C illustrates another embodiment of the fin design in a predesigned digital library of fins.
FIG. 4D illustrates another embodiment of the fin design in a predesigned digital library of fins.
Figure 4E:
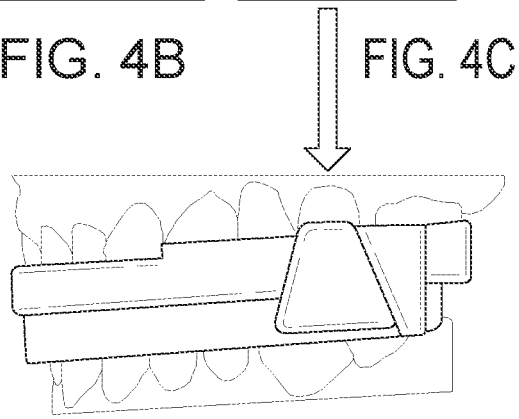
FIG. 4E illustrates that a fin design from the library is incorporated into an embodiment of the disclosed mandibular advancement device.

In one embodiment, the fins are selected from a predesigned digital library of fins. FIG. 4 shows additional embodiments of the fin design. FIGS. 4A-4D show some of the embodiments used in a fin library. In some embodiments, a designer calls from a library of fin designs, for example those shown in FIGS. 4A-4D, select one fin type (for example that shown in FIG. 4C), and place onto the custom patient splint design, as shown in FIG. 4E.

Figure 5:
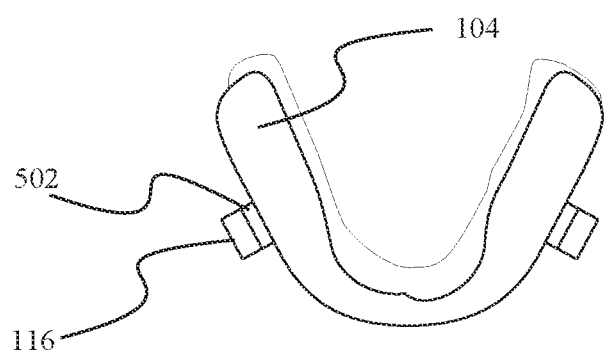
FIG. 5 illustrates an embodiment of the disclosed mandibular advancement device where there exists a gap between the lower fin and the lower splint.

In some embodiments, for example that shown in FIG. 5, there exists a gap 502 between the lower fin 116 and the lower splint 104. While the fin 116 is attached to the splint 104 at the base, the fin 116 protrudes slightly outwards before protruding upward. In some embodiments, a corresponding gap exists between the upper fin 114 and the upper splint 102. The gap 502, if present, is designed into the device based on the prescription and patient anatomy and comfort. The gap 502 further allows for the side to side motion of the lower jaw with respect to the upper jaw.

Figure 6:
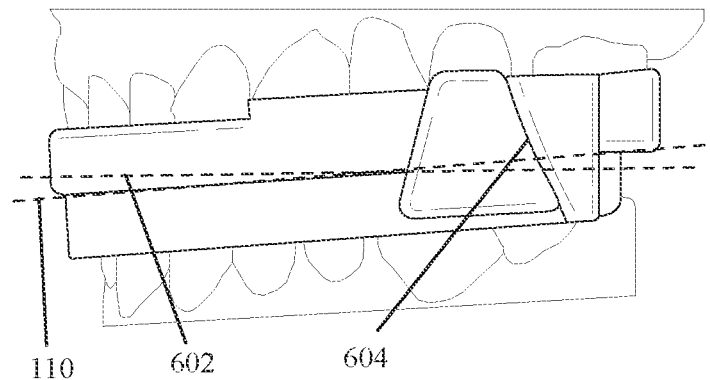
FIG. 6 illustrates varying the plane of the splint with respect to the occlusal plane.

When the device is worn by a patient and the patient's mouth is closed, the bottom surface of the upper splint and the top surface of the lower splint contact each other along the curve of the device, i.e., the arch of the mouth. The two surfaces contact each other along the plane of the splint. In one embodiment the opposing surfaces of the splint are designed such that the plane of the splint equals the occlusal plane. In some embodiments the plane of the splint is at an angle to the occlusal plane. FIG. 6 illustrates the ability to design devices in varying degrees of angle of the plane 110 of the splint to the occlusal plane 602. In CAD, the angle of the plane 110 of the splint can be adjusted within the sagittal plane relative to the patient's anatomical occlusal plane 602. Moreover, the angle of the plane 110 can be adjusted within the frontal plane relative to the patient's occlusal plane 602.

Both adjustments are useful to the clinician to affect changes to the relative positioning of the mandible and maxillae. The path of the movement of the upper and lower arches, for the opening and closing of the mouth, is affected by the engagement surface 604, i.e., where the contact surfaces 202 and 204 meet. If the engagement surface 604 is not properly designed, then the upper and lower arches open and close along an unnatural arc, causing pain for the patient. In manufacturing the disclosed devices 100, the natural arc of the patient's jaw movement is taken into account in the digital design. The engagement surface 604 is then designed to fit the natural arc.

In some embodiments, the device 100 is made of transparent materials, for example transparent plastic, to allow the clinician to see the patient's dentition through the device 100 to ensure good fit. Thus, in some embodiments, the clinician can insert a generic device 100 into the patient's mouth and mark the various measurements on the transparent device 100 instead of preparing a dental impression. In other embodiments, a transparent device 100 is prepared first, and relatively inexpensively, and the fit is tested before a more expensive and permanent device is manufactured.

In some embodiments the fins vary in length. In certain embodiments, the fins are adjusted to the patient's open mouth dimensions. In some embodiments, the fins vary in length related to the opposing fin to optimize the length required to maintain mandible offset position while considering comfort such that each fin is the same length or a fraction of the length of the opposing fin. The sum of the heights of an upper fin 114 and lower fin 116 is the total range of contact along the engagement surface before the two splints are separated. At the point of separation, the two splints do not exert pressure on each other and do not provide any jaw offset. In some embodiments, the upper fin 114 and lower fin 116 are of equal heights. In these embodiments, the total range is optimized while minimizing the height of either fin. The ratio of the heights of each fin can also be adjusted for patient comfort or clinical reasons.

In some embodiments, the thickness of each fin can be adjusted to apply more or less pressure against the cheek. The pressure on the cheek stimulates the body to adjust the muscles in the mouth area, e.g., the airway muscles, for patient comfort or clinical reasons.

In one embodiment the device embeds one or more structural features that create strength using less material. In some embodiments the structural feature is made from a single material. The term "embed" as used herein refers to a single material with design geometries or purposefully milled slots or other geometries that enable another material to be added as a support member, in the same way a rebar can strengthen a concrete block. In some embodiments the structural feature is made from a combination of materials, such a metal alloy. In some embodiments the metal or metal alloy is in the shape of a ball clasp, retention wire, or treatment wire. In some embodiments the treatment wires comprise of wires to aid in a clinical result deemed important by the practicing doctor, such as retention wires, alignment wires, or a tongue behavior modification wire such as spikes or barbs to affect tongue thrust.

A patient inserts the disclosed devices 100 into the patient's mouth before sleep and removes them after sleep. The devices should be retained in the mouth snugly enough so that the device does not fall out while the patient is sleeping. However, the fit cannot be too snug so that the patient cannot easily remove the device after waking up. The retention of the device 100 in the mouth is achieved using a combination of one or more of a variety of retention devices and gaps in space between the device and tissue.

Figure 7:
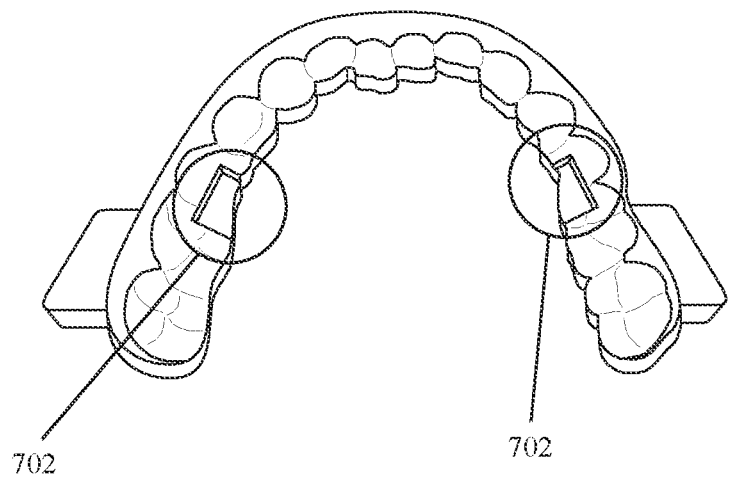
FIG. 7 shows the occlusal side of a splint with cutouts designed into the device to accurately place ball clasps.

In one embodiment the device is retained onto the teeth of a patient using patient specific retention arms. In some embodiments, the retention arms replace or improve the classic use of ball clasps. In the embodiments where ball clasps are used, space for their placement can easily be designed into the splint. In one embodiment, FIG. 7 shows the occlusal side of a splint with cutouts 702 designed into the device to accurately place ball clasps.

Figure 8A:
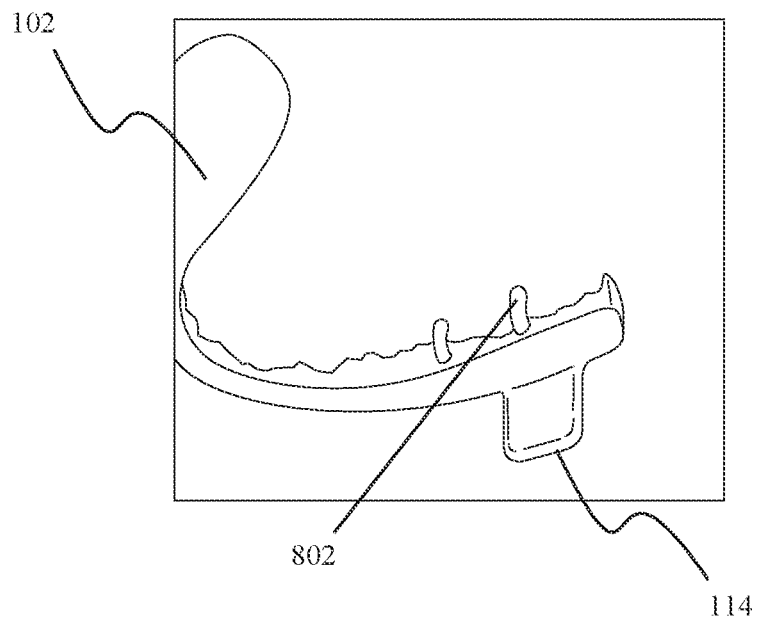
Figure 8B:
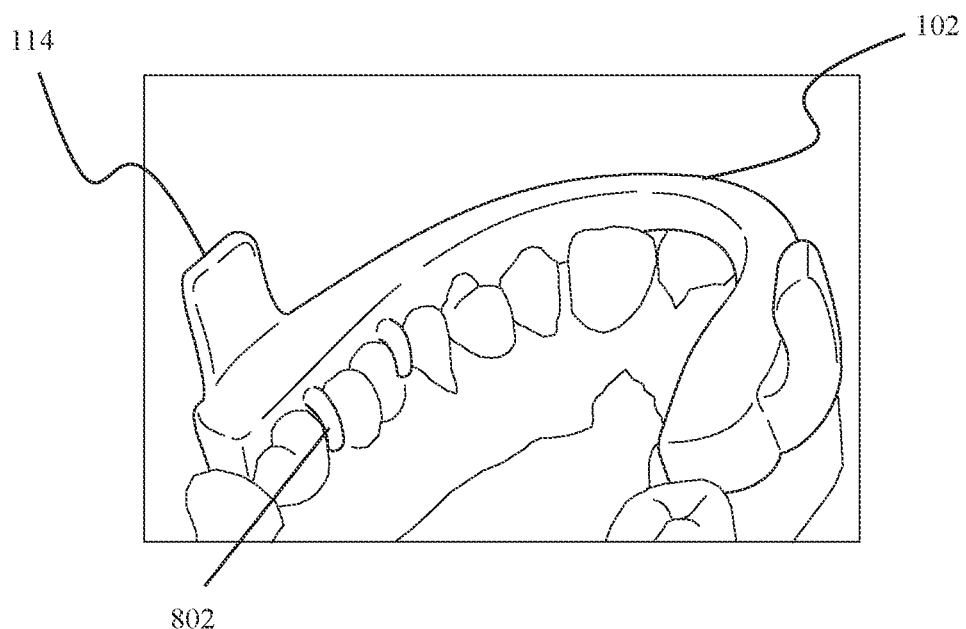
FIG. 8B shows the graphics of how the upper splint and the retention arms fit into the mouth of the patient.

In some embodiments, for example that shown in FIG. 8, the device 100 comprises retention arms 802, built into either or both of the upper splint 102 and lower splint 104. The retention arms 802 allow for a more secure placing of the splints into the mouth. FIG. 8A shows a free standing upper splint 102 with the retention arms 802, while FIG. 8B shows the graphics of how the upper splint 102 and the retention arms fit into the mouth of the patient. In some embodiments, the retention arms 802 take on the shape of the classic ball clasp, while in other embodiments, the retention arms 802 perfectly conform to the patient's anatomy to optimize strength and surface area for retention while allowing for maximum space for the tongue.

In some embodiments, a gap is designed between a particular device surface and one or more surfaces of a patient's anatomy. A purpose of the gaps is to allow the device 100 to be installed easily, stay retained under normal conditions, and be removed easily as well. In some embodiments, the gap is uniform across the entire contact region between the device and the patient's tissue. In other embodiments, the gap is strategically placed with properly designed spacing to provide easy installation of the device in the mouth, optimal device retention onto the patient's dentition, or ease of use of the device. The gap is easily programed into the CAD digital design. Because the disclosed device can be prepared quickly and inexpensively, the clinician or the designer can experiment with a series of different gap placings until the best fit is obtained.

It is possible, through a series of steps, called titration, to choose the device having the most clinically relevant mandibular advancement setting for the patient. Thus, in another aspect, disclosed herein methods of selecting a mandibular advancement device for a patient, the method comprising:

a) obtaining two or more upper splints of the mandibular advancement device, wherein each upper splint comprises one or more upper fins, wherein each upper fin is located at a distance UD from back of the upper splint, and wherein the distance UD of any of the two or more upper splints is different than the distance UD of any other of the two or more upper splints; and obtaining two or more lower splints of the mandibular advancement device, wherein each lower splint comprises one or more lower fins, wherein each lower fin is located at a distance LD from back of the lower splint, and wherein the distance LD of any of the two or more lower splints is different than the distance LD of any other of the two or more lower splints;

b) choosing a combination of one upper splint and one lower splint for the patient;

c) observing the clinical outcome of the chosen combination of one upper splint and one lower splint;

d) choosing a different combination of one upper splint and one lower splint for the patient if the clinical outcome of step c) is unacceptable; and e) repeating steps b)-d) until an acceptable clinical outcome is obtained.

Once a digital scan of the patient's dentition is obtained, a number of upper and lower splints are milled for the patient. Each of the upper and lower splints has a different fin offset setting. The clinician chooses one set of upper and lower splints for the patient. If the patient's condition is not improved sufficiently, the clinician then chooses another set of splints. This process is continued until a set of splints providing the best clinical outcome is chosen. An advantage of the devices and methods disclosed herein is that by digitally designing the splints and automatedly manufacturing them, several splints can be prepared relatively quickly and inexpensively. Further, the digital design allows for a precise positioning of the fins. A more effective mandibular advancement can then be obtained than by using a hand-milled and hand-cranked device.

In some embodiments, the titration settings provide for a flexible positioning of the fins in the mouth in the mesial-distal direction. In some embodiments, the fit of the device 100 on a patient is titrated through the use of devices 100 with varying distances 208 and 210 (see FIG. 2). In certain embodiments, the device 100 is milled directly from a CAD file such that the accuracy of the data from the impression of the patient's anatomy, the fit of the device to that data, and the design of the device are precisely transferred to the milling machine. This enables very precise design adjustment in positioning each of the fins in the splint, i.e., the measurement of the distances 208 and 210, and in their position relative to each other in a reproducible and manufacturable way.

For example, in one embodiment, three different upper splints 102 were manufactured having increasingly longer distances 208, i.e., longer fin offset. Also, two different lower splints 104 were manufactured having two different distances 210. Thus, pairing one lower splint 104 with one upper splint 102 provided one jaw offset, while pairing the same upper splint 102 with a different lower splint 104 provided another jaw offset, and so on.

An illustrative example is shown in Table 1. To compile this table, five different upper splints 102 were prepared having 0.0 mm, 1.0 mm, 2.0 mm, 3.0 mm, and 4.0 mm fin offset (distance 208), respectively. Also, four different lower splints 104 were prepared having 0.0 mm, 0.5 mm, 1.0 mm, and 2.0 mm fin offset (distance 210), respectively. The combination of the two different splints can provide a jaw offset ranging from 0.0 mm to 6.0 mm, as shown in Table 1, where U-1 to U-5 are the upper splint offsets (shown in parentheses) and L-A to L-D are the lower splint offsets (shown in parentheses).

TABLE 1

|  | U-1 (0.0 mm) | U-2 (1.0 mm) | U-3 (2.0 mm) | U-4 (3.0 mm) | U-5 (4.0 mm) |
| --- | --- | --- | --- | --- | --- |
| L-A (0.0 mm) | 0.0 mm | 1.0 mm | 2.0 mm | 3.0 mm | 4.0 mm |
| L-B (0.5 mm) | 0.5 mm | 1.5 mm | 2.5 mm | 3.5 mm | 4.5 mm |
| L-C (1.0 mm) | 1.0 mm | 2.0 mm | 3.0 mm | 4.0 mm | 5.0 mm |
| L-D (2.0 mm) | 2.0 mm | 3.0 mm | 4.0 mm | 5.0 mm | 6.0 mm |

Thus, twenty different mandibular advancements can be obtained with only nine different splints, four lower splints and five upper splints.

Depending on the clinician's prescription need, the clinician chooses any reasonable value for the offset of the upper fin relative to the lower fin, and as many offsets as the clinician desires. Since the digital manufacturing process accurately and precisely reproduces the splints, the combination of splints is repeatable, regardless of when the clinician orders several splints or splints with other offset distances.

Another advantage of the disclosed splint combination is enabling the creation of the same offset with different combinations of upper and lower splint positions. For example, as shown in Table 1, a 3.0 mm offset may be created using three different combinations of upper and lower fins (L-A/U-4, L-C/U-3, and L-D/U-2). Varying the combined position of the two fins allow better alignment of the fins within the mouth for reasons of patient comfort and clinical requirements.

Figure 9:
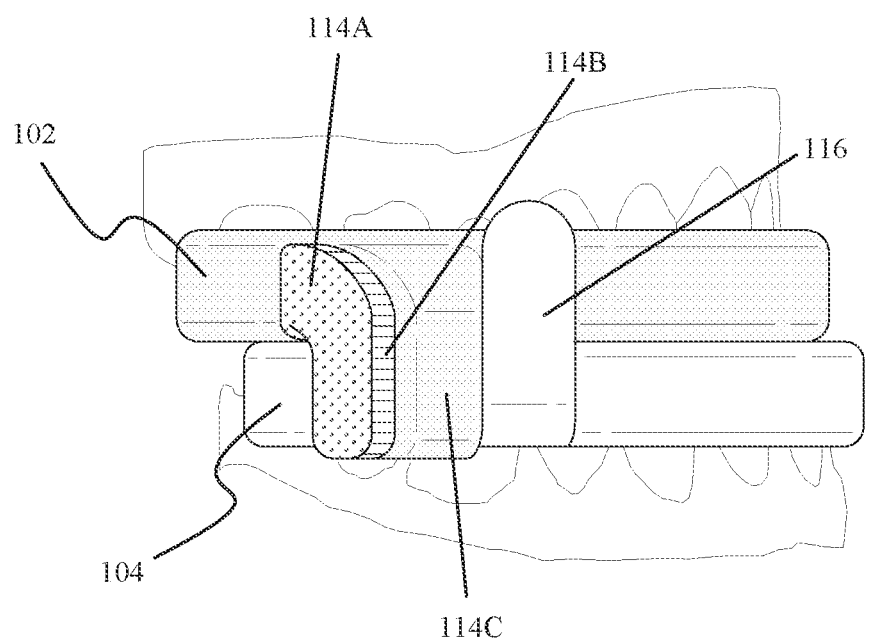
FIG. 9 shows the mechanism of titration when using multiple upper splints with one lower splint. Each illustrated upper fin belongs to a separate upper splint

FIG. 9 illustrates the titration. Three separate upper splints 102 are provided, one having an upper fin offset of 1 mm (114-A), one having an upper fin offset of 2 mm (114-B), and one having an upper fin offset of 3 mm (114-B) (FIG. 9 shows all three of these upper splints superimposed on each other for illustration purposes. In actuality, they are separate splints.) One lower splint 104, having a lower fin offset of 0.5 mm (116) is also provided. Not shown is a lower splint 104 having a lower fin offset of 0 mm. The following combinations of splints provide the mandibular advancements of Table 2.

TABLE 2

| Upper▶ Lower▼ | 1.0 mm | 2.0 mm | 3.0 mm |
| --- | --- | --- | --- |
| 0.0 mm | 1.0 mm | 2.0 mm | 3.0 mm |
| 0.5 mm | 1.5 mm | 2.5 mm | 3.5 mm |

In another aspect, disclosed herein are methods of reducing partial constriction of airway during sleep for a patient, the method comprising identifying a patient in need thereof; and administering to the patient the mandibular advancement device as disclosed herein.

In another aspect, disclosed herein are methods of manufacturing a mandibular advancement device, the method comprising obtaining measurements from a patient's dentition; digitally designing a mandibular advancement device; and milling the mandibular advancement device. In some embodiments, the obtaining measurement step comprises obtaining a dental impression.

While the methodology disclosed herein can be practiced through numerous different, and varied, steps, the steps can be thought of as falling into at least three separate, yet connected, stages. First, a health care provider (HCP) examines the patient and obtains an impression of the patient's dentition, and models the bite by taking a bite impression in one or more positions of the mandible relative to maxilla. The relative position of the jaw bones also includes the position of the condyle in the mandibular fossa. The impressions can be taken traditionally with dental impression material and poured up in stone either at the HCP office or at the manufacturing laboratory or site (MFG). Additionally, the HCP may digitally capture the patient dentition, bite (for example relative bite position) and anatomy and send the resulting data set to the MFG. The HCP may also capture the position of the mandible relative to the maxilla at several positions such that a range of motion can be modelled from which an ideal new position for the mandible, which was not captured in the clinic, can be created in the CAD software. In some embodiments, the HCP also captures data regarding the patient's anatomy. These data may include cone beam computer tomographic (CBCT) images of the temporomandibular joint (TMJ), facial landmarks, airway anatomy, and the like.

Then, based on the patient's needs and anatomy, the HCP selects several clinical options, discussed fully below, for the particular device of interest for the patient. Second, the HCP communicates these clinical options to the MFG. The MFG creates a computer aided design (CAD) of the device, having the selected clinical options. Third, the design is communicated to an automated manufacturing machine, which creates the selected device from a block of an appropriate material. Other machines can then install other accessories that cannot be manufactured as a single contiguous unit along with the device. The CAD process may create several devices from the same data set, each device designed to serve a different aspect of the treatment plan, such as nighttime treatment of sleep apnea or bruxing, or daytime treatment for pain relief or aesthetics, where the device places the mandible in a different position relative to the maxilla for a specific outcome related to the treatment plan.

In some embodiments, the block is made up of a solid material. In certain embodiments, the block is a polymeric block. In other embodiments, the block is made of a natural substance, for example metal, wood, natural resin, natural rubber, and the like. In other embodiments, the block is made of synthetic polymeric material, having either one type of monomer or two or more co-polymers.

The automated fashion by which the dental devices are prepared allow for a multitude of different devices, having different features, to be prepared rapidly and economically, where the devices are identically manufactured. This allows for the patient and the HCP to experiment with a number of different option to see which one fits the patient's mouth and dentition better. This process cannot be effectively done using the current technologies because the current dental devices are prepared artisanally by hand, which introduces variations into the manufactured devices, even when they are prepared from the same exact set of requirements.

Thus, in one aspect, disclosed herein are methods of manufacturing a dental device, the method comprising:
  obtaining a set of clinical options from a HCP;
  creating a first data set from the set of clinical options;
  communicating the data set to a computer aided design (CAD) software;
  preparing a digital design for the dental device using the CAD software;
  communicating the digital design to an automated manufacturing apparatus; and
  automatedly manufacturing the dental device.

In some embodiments, the steps of preparing the digital design, communicating the design with the manufacturing apparatus, and manufacturing the device, are repeated for each of the desired devices. In some of these embodiments, however, the same patient data set is used to manufacture the multitudes of devices. In some embodiments, the several devices are used in sequence. For instance, if the mandibular repositioning is meant to include repositioning in various directions, one device may be used to reposition the mandible from a first to a second position, a second device is used to reposition the mandible from the second to a third position, and etc.

In some embodiments, the HCP is a dentist. In other embodiments, the HCP is a dental technician. In other embodiments, the HCP is a sleep disorder specialist. In certain embodiments, the HCP is an individual charged with altering the position of the patient's mandible (e.g., the use of mandibular advancement devices). In other embodiments, the HCP is an individual charged with straightening a patient's teeth (orthodontia) (e.g., the use of braces and the like. In other embodiments, the HCP is a Temporal Mandibular Joint (TMJ) and Disease (TMD) specialist who repositions the mandible to manage pain. In certain embodiments, the patient is a human.

In some embodiments, the presently disclosed methods produce a mandibular advancement device that is worn at night during sleep, while in other embodiments, additional or singular devices are designed to be worn during the day. In still other embodiments, the device can be used 24 hours a day.

Dentition Impression

Obtaining the data regarding the shape of the patient's dentition is well-known to those of ordinary skill in the art. In some embodiments, the HCP obtains the dentition impression using trays filled with impression materials. The impression is then used to create a plaster model identical to the patient's dentition.

In some embodiments, the HCP provides photographs of the patient's dentition. A computerized three-dimensional (3D) image of the patient's dentition can then be prepared. In some embodiments, the patient's dentition is scanned, for example with an intraoral scanner, while in other embodiments, the plaster model of the patient's dentition is scanned. The scanning data is used to create a computerized 3D image of the patient's dentition.

A clinically obtained data set can be obtained from the patient's anatomy using techniques such as, but not limited to, X-ray imaging, dental impressions, intraoral scanning, cone bean computed tomography (CBCT), palpitations of the area around the jaws, visual inspection of the dentition, or patient testimony. The term "anatomy" includes any patient data that refers to hard or soft tissue, or specific features that describe that tissue, that may include well known landmarks such as molar cusps, height of contour, anatomical planes, facial landmarks or descriptive values such as arch shape, tongue size, or Malampatti score and the relationship between the hard and soft tissue to appearance or function. The data set is then used to create a patient specific prescription that is precisely implemented into the treatment device via a CAD/CAM platform and/or a matrix-generated prescription of various option, such as the one disclosed in U.S. patent application Ser. No. 15/416,715, the entire disclosure of which, including any drawings, is incorporate by reference herein.

In some embodiments, patient testimony includes descriptions of symptoms related to sleep breathing disorders, such as sleep apnea, snoring, upper airway resistance syndrome (UARS) or symptoms related to malpositioning of the mandible affecting the patency of the airway or discomfort at the temporal mandibular joint (TMJ) realized as temporal mandibular disorder (TMD). The mandible is capable of being positioned in the anterior-posterior direction (AP), being positioned in the vertical dimension (perpendicular to the occlusal plane), or rotate around an axis contained in the occlusal plane. Sometimes the comparison to an airplane or a ship having the three axes of rotation of pitch, yaw, and roll is a useful analogy.

In some embodiments, an HCP provides instructions based on the current position of the patient's mandible and a desired treatment position. The desired treatment position can be determined by many methods, including positioning the mandible in an open and protruded position using a George Gauge, ProGauge, Airway Metrics or other like gauges. Additionally, there are methods that use enunciation of numbers such as "sixty six" to provide a guide for a treatment position. The HCP can also use airway analysis using CBCT software in the two positions (current and desired), evaluate the alignment of the condyle in the fossa for TMJ positioning or use X-ray imaging for anatomical measurements. For example, the position of the condyles for the left and right side of the patient could be measured relative to an established healthy position. In other embodiments, the HCP may also find an optimal position for the mandible using heart rate variability, or other systemic body variables. The difference in the left and right positions relative to the treatment position can then be documented and written into the prescription creating the proper protrusion (symmetrical or asymmetrical), vertical repositioning, and any other angular components of the mandibular position. The positioning of the mandible may also meet patient needs concerning the aesthetics of the face and the impact of a new mandibular position to the look of the face.

Selecting Clinical Options

The set of clinical options is prepared based on the HCP's determination of what is required and/or most effective for the treatment of the patient. Thus, the set of clinical options is at times referred to as the "prescription" or "Rx" that the HCP provides for the treatment of the patient.

Throughout the present disclosure, the word "option" or the phrase "clinical option" as it relates to the selectable options for a dental device, refers to a category of features. For example, titration option refers to the category of available titration features. Titration options serve to create the method of advancement of the mandible relative to the maxilla. Each particular feature under an option is a "selection." Thus, the HCP chooses a selection under an option.

After examining the patient's dentition and oral anatomy, the HCP obtains information regarding the shape of the patient's dentition or the range of motion of the patient's jaw. The range of motion includes, but is not limited to, rotational and translational movements of the mandible, such as protrusive movement, vertical movement, lip competency (i.e., the extent a person can separate their jaws while keeping the lips closed), or golden proportions (i.e., the aesthetically accepted ratios of teeth size to facial dimensions and symmetry). Commonly, this is done by generating an imprint of the dentition on a polymer or dental impression material. In other embodiments, the data regarding the shape the dentition is obtained by analyzing photographs of the dentition, or by a machine reading the contours of the dentition.

Next, the HCP selects a series of clinical options for the dental device. These clinical options relate to the material that makes up the dental device, the mechanism of titration, and other physical features of the device. These clinical options are described in detail below.

In some embodiments, the selection of the clinical options is through a web portal. In these embodiments, a website is provided for the HCP to communicate the clinical options with the MFG. In some embodiments, the website provides a questionnaire where the HCP provides a written response to questions relating to each option. In other embodiments, the clinical options are listed with a radio button next to each. The HCP chooses the desired option by clicking on the appropriate radio button. In yet other embodiments, the HCP selects the desired option from a drop-down window, listing all the available selections for that particular option.

In some embodiments, the selection of options is intelligently organized. By "intelligent organization" it is meant that when the HCP makes an initial selection, then only groups of subsequent options that create a viable device within the initial selection are enabled. For example, selecting elements of contradictory, weak or unsafe designs are not allowed. The final grouping of the selections along with the patient information and HCP's approval culminate in the prescription. In certain embodiments, the intelligent organization of the selection options include the availability of only those options for a particular selection that comply with regulatory requirements.

In some embodiments, the set of clinical options comprise two or more clinical options selected from the group consisting of titration mechanisms, titration accessories, splint design, retention mechanisms, splint material, and fin or strap design or sleeve (e.g., a covering for a fin). In certain embodiments, the clinical options include other features not enumerated herein.

"Titration" is the process of adjusting the relationship between the mandible and the maxilla for a desire outcome (also referred to as "calibration"), such as relief of symptoms due to obstructive sleep apnea (OSA). Currently, examples of the titration techniques include the threaded screw system on a device, where the patient or the HCP adjust or turn a small screw, which causes a portion of the dental device to move to a position dictated by the HCP (U.S. Pat. No. 6,604,527); or changing of straps of different lengths (U.S. Pat. No. 5,365,945). A novel method of titration is disclosed in the above-incorporated International Publication WO 2015/103084. Portions of the disclosure of the publications listed in this paragraph related to the adjustment mechanism are incorporated by reference herein.

"Retention" is the process of fitting a device to the dentition, such that the device has a tight enough fit to be efficacious, yet has a loose enough fit to be comfortably worn by the patient. Retention may also be optimized to minimize the amount of tooth movement or bite changes caused by wearing a device the imparts forces on the teeth and relative position of the mandible and maxilla to each other.

"Titration mechanism" is a component or property of the device, that through adjustment, the upper and lower arch splint relative position can be affected to achieve a patient outcome. For each mechanism, a number of "titration accessories" is available, by way of which the titration is carried out. These accessories are projections or additions attached to a basic splint. In some embodiments, the titration accessory is selected from the group consisting of an electronic or microelectronic device, a "smart" accessory (i.e., an electronic device that obtains data and communicates the data with another electronic device), affixed sleeve, removable sleeve, straps, anterior hinge, short or long Herbst hinge, jack screw, and Herbst hinge in combination with jack screw, or any other appliance accessory now known or designed in the future. In some embodiments, the accessory is separately manufactured from that of the base dental device. In these embodiments, the accessory itself is attached to the device after the manufacturing of the device. In other embodiments, the accessory is part of the unitary design of the device. In these embodiments, the accessory comes to being at the same time the device is manufactured. For example, a fin, a strap, a hinge, a screw, etc., and combinations thereof, are titration accessories.

In some embodiments, the titration mechanism is selected from the group consisting of microtitration series, jack screw titration, Herbst hinge titration, anterior hinge titration, strap titration, mechanical hook, and combinations thereof.

"Microtitration series" refers to the titration procedure disclosed in the above-incorporated International Publication WO 2015/103084, particularly in Paragraphs [0051]-[0061], which paragraphs are explicitly incorporated by reference herein. Through the use of the microtitration mechanism, a number of upper and lower splints having fins are manufactured for the patient. Each of the upper and lower splints has a different fin offset setting. The clinician chooses one set of upper and lower splints for the patient. If the patient's condition is not improved sufficiently, the clinician then chooses another set of splints. This process is continued until a set of splints providing the best clinical outcome is chosen. In one embodiment, the HCP may start with one titration mechanism and then switch one or both splints to incorporate another mechanism. For example, the upper arch could start with the "Jack Screw" and then be traded out for the microtitration upper splint, which has a lower profile and is more comfortable.

"Jack screw" (also known as "expansion screw") titration refers to a system of titration where the movable parts of the dental device are connected by a screw. A nut is provided, whereby the turning of the nut causes the movable parts to move with respect to each other so that the parts either come closer together or are moved further apart. An example of a jack screw titration is shown in FIGS. 15a and 15b of U.S. Pat. No. 6,604,527 and the corresponding discussion in the specification thereof (incorporated by reference herein).

"Herbst hinge titration" is well-known to the skilled artisan. The hinge comprises a smaller cylinder that fits within a larger cylinder. The user can determine the extent to which the smaller cylinder can extend out of the larger cylinder, thereby limiting the extent of separation of the two cylinders. When one cylinder is attached to, for example, an upper splint of an advancement device and the other cylinder is attached to the lower splint, then the two pieces can be separated by a prescribed distance. By lowering the distance, the user can titrate the device. A discussion of the Herbst device is found, for example, in Vela-Hernandez et al., J Clin Orthod. 2004 November; 38(11):590-9 ("Clinical management of the Herbst Occlusal Hinge appliance"). A Herbst hinge titration may also include a set of fixed bars that are swapped out for different protrusion levels.

In some embodiments, the titration mechanism is a hybrid mechanism. In these embodiments, two or more of the above mechanism, or in combination with other mechanism used in the art, are combined. An example of a hybrid titration mechanism would be the combination of microtitration series with expansion screw. An example of this type of a combination device is disclosed in the International Publication No. WO 2017/132638 (with a specification substantially equivalent to that of U.S. Provisional Application Ser. No. 62/533,420, incorporated by reference herein in its entirety, including the drawings. For instance, the fin location of one of the splints, e.g., upper or lower, is changed by replacing the splint, as in the microtitration series, while the fin location of the other of the splints is changed by the use of a screw.

In some embodiments, once the HCP has determined the titration methodology, the HCP can then pick the desired titration accessory to affect the chosen methodology. In some embodiments, the titration accessory is selected from the group consisting of affixed sleeve, removable sleeve, straps, anterior hinge, short or long Herbst hinge, jack screw, Herbst hinge in combination with jack screw, and combinations thereof.

An "affixed sleeve" is a protrusion immovably attached to the dental device. The location of the protrusion on the splint, and more specifically the relative positions of the sleeves on the upper and lower splints of the dental device, are fixed. An example of the affixed sleeve embodiment is found, for example, in FIGS. 7 and 6 of U.S. Pat. No. 6,604,527 and the corresponding discussion in the specification thereof (incorporated by reference herein).

A "removable sleeve" is a covering that fits over an affixed fin on a splint of a dental device, thereby changing the thickness of the fin. Consequently, the relative positions of the upper and lower fins are changed and the two splints of the device are located at a different distance from each other than without the sleeve. A number of sleeves having different thicknesses can be prepared for each fin. An embodiment of the removable sleeve is disclosed in the International Publication No. WO 2017/132638 (with a specification substantially equivalent to that of the U.S. Provisional Application Ser. No. 62/289,131, incorporated by reference herein, particularly Paragraphs [0015]-[0040] and the drawings.

In one aspect provided herein is a digitally designed and milled mandibular advancement device comprising an upper splint and a lower splint, wherein the upper and lower splints independently further comprise one or more fins. Also disclosed, to be used with the device, are a plurality of sleeves, each pair of sleeves having a unique thickness and/or rake angle, and where the sleeves fit over the fins.

Thus, disclosed herein are sleeves for use with a fin of a mandibular advancement device, the sleeve comprising:
 a shell, having a wall defining a hollow interior,
  wherein the wall encloses the hollow interior on all sides except one, leaving an opening at one end of the body;
  the wall has a thickness in the range of from about 1 nm to about 5 mm;
  the hollow interior comprises approximately the same size and dimensions as the fin of the mandibular advancement device.

In some embodiments, the sleeved fins on the splints provide accurate increments of advancement of the lower jaw for titration of the mandible. The terms "dental splint" and "splint" as used herein refers to several types of orthodontic devices that are designed to address dental problems such as loose teeth and bruxism, in addition to problems with snoring and apnea. More specifically, the term "splint" refers to an upper or lower splint, having sleeveless fins, which splint is uniquely designed to fit over a patient's dentition. Thus, as is disclosed further below, the present disclosure distinguishes between a "sleeveless-fin splint," which is a splint that fits over the patient's dentition but the upper and lower fins do not make sufficient contact to provide the desirable extent of mandibular advancement, and "sleeved-fin splint," where presently disclosed sleeves have been placed over the upper and lower fins of the splints, where the increased thickness afforded by the sleeves causes mandibular advancement when the splints are worn by the patient.

A patient in need of the disclosed mandibular advancement devices wears the upper splint on the upper dentition and the lower splint on the lower dentition during sleep. The splints are designed to remain attached to the dentition until the patient removes them. The sleeved fins of the upper and lower splints cause a precise placement of the mandible in relation to the maxilla. The mandible is caused to stay in a forward position and does not relax and fall back. The airway constriction during the sleep is thereby minimized.

In one embodiment the device creates an offset between the upper and lower splints by using upper and lower sleeved fins as boundary surfaces to restrict movement while the mouth is closed or reasonably opened, e.g., opened to the same extent that the mouth opens during sleep.

In some embodiments, the splints with sleeveless fins, disclosed herein were digitally designed and then milled as a single unit. In some of these embodiments, a computer aided design (CAD) process were used to design and manufacture the mandibular advancement devices disclosed herein. Plaster models of the patient's upper and lower dental impressions were first obtained using well-known techniques in the art. Then, scans of the plaster models were imported into the CAD software. In other embodiments, the 3D files of the patient's impression are imported from other sources, such as a direct scan of the patient dentition using an Intra Oral Scan (IOS) Device, e.g., the 3M TruDef™ scanner, or a direct scan of the impression from either an IOS or Cone Beam Computed Tomography (CBCT) device. In these embodiments, the files enable the design of the mandibular advancement splint in 3D space in a CAD software such as 3-Matic by Materialise™.

In other embodiments, the different components of the disclosed devices, for example the splint, the fins, the fin sleeves, the retention arms, etc., are milled or manufactured separately and then attached together after the manufacturing. This approach allows for the use of interchangeable parts. The design and manufacturing processes are described in the co-pending U.S. application Ser. No. 15/416,715, the entire disclosure of which, including the drawings, and especially Paragraphs [0012]-[0053], inclusive, are hereby incorporated by reference.

In some embodiments, a unique single set of upper and lower splints with sleeveless fins are prepared for each patient. The patient is then provided with a library of sleeves that fit over the fins. By changing the sleeves, the patient or the healthcare provider can change the extent of mandibular advancement. This approach to the manufacture and use of mandibular advancement devices provides for a less costly, easier to use, and easier to manufacture approach to mandibular advancement.

In one embodiment, the splint is designed to comfortably fit on to a patient's upper and lower arches, and maintain a maximum amount of space for the tongue. The sleeved fin keeps the mandible advanced forward per a doctor's prescription while still allowing the patient to reasonably open their mouth and move their jaw from left to right for comfort. This contact serves as a barrier to keep the lower sleeved fin in a position forward of this fin engagement surface.

The disclosed devices can be made from any material that can withstand the oral environment for an extended period of time, for example overnight. Furthermore, the material can be any material that is capable of being milled to form the devices disclosed herein. Examples of materials include plastics and other polymers, whether hard or soft, transparent or opaque. Some suitable polymers include, but are not limited to, a polyetheretherketone (PEEK), polystyrene, polyvinyl chloride, rubber, synthetic rubber, or an acrylate polymer, such as a polymer made up of methyl methacrylate, methyl acrylate, ethyl acrylate, 2-chloroethyl vinyl ether, 2-ethylhexyl acrylate, hydroxyethyl methacrylate, butyl acrylate, butyl methacrylate, or trimethylolpropane triacrylate (TMPTA).

In some embodiments, a lower splint is provided with sleeveless fins. In some embodiments, both the upper and lower splints comprise sleeveless fins configured to receive a sleeve. In other embodiments, one of the upper or lower splint comprises sleeveless fins configured to receive a sleeve, while the other of the upper or lower splint is configured to make contact with the sleeved fin of the other splint. That is, the fin thickness and/or rake angle of one splint can be varied while the fin thickness and/or rake angle of the other splint is kept constant. While the disclosure here is in the context of the fins on a lower splint, the skilled artisan recognizes that both the upper and the lower splints, or either of the upper or lower splints, can be made to exhibit the use of the sleeves disclosed herein.

In an embodiment of the lower splint, the right fin is a sleeveless fin that is configured to receive a fin. The left fin is a sleeved fin, where a sleeve has been placed over the fin. The sleeve increases the thickness of the fin and can provide a rake angle that is different than that of the fin, or that of other sleeves. In some embodiments, the rake angle is 90°, while in other embodiments, the rake angle is between about 20° to about 80°, for example, an angle selected from the group consisting of about 20°, about 25°, about 30°, about 35°, about 40°, about 45°, about 50°, about 55°, about 60°, about 65°, about 70°, about 75°, and about 80°. In other embodiments, the rake angle is between about 100° to about 160°, for example, an angle selected from the group consisting of about 100°, about 105°, about 110°, about 115°, about 120°, about 125°, about 130°, about 135°, about 140°, about 145°, about 150°, about 155°, and about 160°.

By "about" a certain value it is meant that the stated value comprises the range of values within ±25%, ±20%, ±10%, or ±5% of the stated value. Thus, by way of example only, if a distance is given as "about 5 mm," the range of distances between 3.75 mm (5-25%) to 6.25 mm (5+25%) is envisioned.

In some embodiments, each sleeve comprises an outer shell, which defines a hollow interior. Thus, the sleeve has an open end, where the hollow interior is accessed, and a closed end opposite the open end. The dimensions of the hollow interior are such that the sleeveless fin fits inside the hollow interior. When worn over the fin, the open end of the sleeve abuts the splint, whereas the closed end is distal to the splint.

In some embodiments, the fit between the sleeve and the fin is such that when the sleeve is placed over the fin, the sleeve is substantially immobile with respect to the fin. By "substantially immobile" it is meant that the movement of the sleeve with respect to the fin is not perceptible by the naked eye (that is to say, the sleeve does not "rattle" when it is placed over the fin).

In some embodiments, the closed end of the sleeve is curved away from the plane normal to the plane defined by the rim of the open end. In certain embodiments, the curvature of the sleeve approximates the curvature of the patient's mouth, whereas in other embodiments, the curvature approximates that found in the mouth of an average patient. The curvature prevents the closed end of the sleeve to bore into, or unduly rub against the inside of the patient's cheeks and allows for greater comfort for the patient when the device is worn.

The sleeve, and the corresponding sleeve for the upper sleeve, can each have one of a multitude of designs and shapes. In one embodiment, the sleeves are selected from a predesigned digital library of sleeves. In some embodiments, a designer calls from a library of sleeve designs and selects one sleeve type. The design is selected based on the patient's need and the geometry of the patient's dentition and mouth. A set of sleeves are then prepared having the desired sleeve design. The sleeve is then placed on the fin of the customized patient splint design.

The outer shell of the sleeve has a thickness. In some embodiments, the thickness is uniform throughout the perimeter of sleeve. In other embodiments, the thickness varies from location to location in order to enhance the strength of the sleeve. In certain embodiments, at least the thickness along the contact surface of sleeve with sleeve varies from one sleeve to another in a set of multiple sleeves prepared for the same patient. Thus, by varying the thickness of either or both of sleeves, the extent of mandibular advancement is varied.

In some embodiments, the thickness can be varied, either within a sleeve or from one sleeve to another, for example, from a 1 nm to 5 mm, or from 1 µm to 5 mm, or from 1 mm to 5 mm. In some embodiments, the thickness is no more than 4 mm, 3 mm, 2 mm, or 1 mm.

Various locking mechanisms are contemplated to secure the sleeve over the fin. In some embodiments, the sleeve is held in place over the fin by a friction lock mechanism. In these embodiments, the tight fit of the sleeve over the fin creates enough friction that the normal use of the device does not dislodge the sleeve from over the fin. In some of these embodiments, corresponding grooves (not shown) on one or both of the sleeve and fin increases the friction between the two pieces.

In other embodiments, the locking mechanism is a key-tab mechanism. The tab mechanism is incorporated into the design of the sleeve. The tab mechanism is separated from the sleeve shell by a gap. The thickness of the gap can be varied, for example, from a 1 nm to 5 mm, or from 1 µm to 5 mm, or from 1 mm to 5 mm. The tab has a length, which is less than the full length of the sleeve. The length can be varied depending on the thickness of the shell, or the hardness of the material making up the sleeve, and in some instances depending on the dexterity of the patient, to provide for a convenient release operation, as discussed below.

At one end of the tab, either the end close to the open end or the end close to the closed end of the sleeve, the tab is connected to the sleeve shell by a living hinge. In some embodiments, the living hinge is proximal to the open end of the sleeve. In some embodiments, the tab comprises a key at the opposite end of the tab from the living hinge. Along the length, and between the living hinge and the key, a fulcrum is located. The position of the fulcrum can be varied to provide the most convenient release operation for the patient.

In some embodiments, the fin comprises a notch. When the sleeve is placed over the fin, the key fits into the notch, thereby holding the sleeve in place. To release the sleeve, the user pushes on the tab at a location between the fulcrum and the living hinge. When the tab is pressed, the key moves in the opposite direction and the key is released from the notch, allowing the sleeve to be removed.

In some embodiments, the tab is located on the lingual side of the sleeve (i.e., the side facing the mouth cavity, or the tongue), whereas in other embodiments, the tab is located on the buccal side of the sleeve (i.e., the side facing the inside of the patient's cheek). In some embodiments, the sleeve comprises at least two tabs, one on the lingual side and one on the buccal side. In other embodiments, the tab (or tabs, if there are more than one tab) are located on the surfaces orthogonal to the lingual and buccal surfaces. In certain embodiments, the tab is located on the surface opposite the contact surface. The presence of more than one tab provides additional locking strength.

In another embodiment of a locking mechanism, the fin on the splint comprises a key button, such as a raised boss. The sleeve comprises a key threshold, which culminates in a key hole. The shape of the key hole matches the approximate contours and size of the key button. In these embodiments, the shape of the key button and the key hole is approximately circular. The key threshold opens at the open end of the sleeve. The threshold provides a friction lock for the key button such that once the sleeve is placed over the fin and the key button is placed inside the key hole, the sleeve does not fall out of place without the user intentionally removing the sleeve.

As discussed above, the rake angle can be modified to be in either neutral, procline, or recline orientation. In some embodiments, the fin is in a neutral orientation and the rake angle is changed by changing the sleeve. In these embodiments, only the sleeve affords a change in the rake angle. In other embodiments, both the fin and the sleeve are oriented in the desired rake angle orientation.

In one aspect, provided herein are nesting sleeves. In some embodiments, different sleeves have different sized hollow interior, such as one sleeve can fit over another sleeve. To titrate the patient, first the smallest of the selected sleeves (a "first sleeve") is put over the fin and the device is tested. if there is a desire to increase the extent of mandibular advancement, then another sleeve, with a larger hollow interior (a "second sleeve"), is placed over the first sleeve, thereby increasing the overall thickness covering the fin. The next sleeve in the set (a "third sleeve") can fit over the second sleeve and increase the thickness yet again.

In some of these embodiments, the thickness of the different sleeves is the same, whereas in other embodiments, the thickness of one sleeve is different than the thickness of another sleeve. In certain embodiments, the thickness of the second and subsequent sleeves on the buccal and lingual sides is kept relatively thin, i.e., 75%, 50%, 40%, 25%, or 10%, of the thickness of the sleeve on the contact surface side. By varying the thickness in this manner, the sleeve bulk in the patient's mouth is kept to a minimum while the mandibular advancement is increased.

In some embodiments, the sleeves having different thickness or different sized hollow interior, have different colors. In certain embodiments, the sleeves are opaque whereas in other embodiments, the sleeves are transparent. In some embodiments where the second sleeve fits over the first sleeve, as discussed above, the sleeves are both transparent and have different colors. In certain of these embodiments, the colors of the first and second sleeves combine to form a new color. For example, and without limitation, in one embodiment the first sleeve is blue and the second sleeve is red. When the second sleeve is placed over the first sleeve, then the combined color will be purple. In these embodiments, the patient or the healthcare provider can quickly determine the extent of mandibular advancement by looking at the color of the sleeved fin.

A "strap" is a rubber or stretchable plastic band that connects the upper and lower splints of a mandibular advancement device, thereby providing mandibular advancement while allowing for a limited motion of the mandible. In some embodiments, the strap is elastic while in other embodiments, the strap is not elastic. In some embodiments, the strap is stretchable while in other embodiments, the strap is not stretchable. An example of a device using straps is the EMA® (Elastic Mandibular Advancement) oral appliance (Glidewell Laboratories, Newport Beach, CA). In some embodiments, the strap is a non-stretchable strap, for example as used with NARVAL™ CC (ResMed, San Diego, CA). In some embodiments, the strap is a link, which is a rigid, non-stretchable, strap, typically made from a rigid polymer or metal.

In some embodiments, the upper and lower splints of a dental device are connected by a frontal, or anterior, hinge. The relative openness of the hinge determines the extent of the device's opening. An example of a device using the anterior hinge is the TAP® (Thornton Adjustable Positioner) series of devices (Keller Lab, Fenton, MO).

While in some embodiments, the HCP chooses the titration methodology first and then chooses the titration accessory, in other embodiments, the HCP chooses the titration accessory first, and then based on the accessory chooses the titration methodology.

In some embodiments, the splint design is selected from the group consisting of a fin, anterior opening, anterior discluder, scalloped occlusal surface, lingual opening, a tapered posterior, a tongue attractor, lingualess, full lingual coverage, edentulous, posterior lingual, anterior lingual, anterior lingualess, and monoblock.

The devices worn by a patient comprise a dentition arc that fits over the patient's dentition. In some devices, the internal space of the arc is empty. In other words, in these devices the splint forms the shape of a "U." These devices are termed "lingualess" devices. (See, for example, SomnoDent® (SomnoMed®, Frisco, TX) and MicrO$_2$® (ProSomnus®, Pleasanton, CA)). In other devices, the posterior portion of the splint, i.e., the ends of the "U" that cover the molars, are connected together to provide additional strength to the device. The anterior space remains empty. These devices are termed "anterior lingualess" devices. In some other devices, termed the "full lingual coverage" design, the splint lacks the empty middle section.

A "posterior lingual" or "partially lingual" design is defined as the design of a dental device that covers the posterior teeth and provides lingual coverage adjacent to the posterior teeth. In this design, the device does not cover the lingual or possibly the labial sides of the front teeth, e.g., the incisors. In some embodiments, the posterior lingual design has an anterior portion that fits behind the front teeth. In other embodiments, the design has no anterior component. The posterior lingual design exerts a different level of retention than other designs, which may be of greater comfort for some patients. This design also enables a structured contoured design, and/or increases the strength of the device while leaving the space behind the anterior teeth minimally covered or not covered at all.

An "anterior lingual" design is defined as the design of a dental device that provides lingual coverage adjacent to the anterior teeth. The anterior lingual design exerts a different level of retention than other designs, which may be of greater comfort for some patients. This design also enables a structured contoured design, and/or increases the strength of the device "Edentulous" designs are used when the patient lacks a complete set of teeth. In an edentulous, or full edentulous, design, the patient has no teeth, and the device is designed for over the edentulous ridge, or for over the dentures. In a partially edentulous design, the device is designed to fit in the adventitious space between the teeth. Additionally, a fully edentuluous design can incorporate dental implant screws with buttons that snap into the device for retention.

In a "monoblock" design, the upper and lower splints are fused together in one piece. A series of monoblock splints can create protrusion increments similar to microtitration but with fused components.

In some embodiments, the retention mechanism is selected from the group consisting of implant-retained mechanisms, metallic ball clasps, plastic ball clasps, dental buttons, soft liner, and a hard acrylic polymer.

Several different materials can be used to make splints using the methods disclosed herein. In general, the splint material has one or more of the following attributes: the material has sufficient strength to move the mandible; the material's malleability and/or compressibility is less than 25% of the desired adjustment distance; the material does not disintegrate in the aqueous environment of the mouth; the material does not leave a repugnant taste in the user's mouth; the material is biocompatible with the patient's physiology; the material is strong enough to withstand the pressure exerted by the jaw bones during use; the material can be additively printed or manufactured and the material can be machine grinded into the desired shape. Some embodiments of methods of manufacturing are disclosed in U.S. application Ser. No. 15/416,715, the entire disclosure of which, including the drawings, and specifically Paragraphs [009]-[0059] of the specification as originally filed, are incorporated by reference herein.

In some embodiments, the splint material option is selected from the group consisting of standard polymethylmethacrylate (PMMA), lined PMMA, high-strength polyetheretherketone (PEEK), polymer produced from polyoxymethylene and acetal copolymers (Duracetal®), glycol modified polyethylene terephthalate (PETg), and a physiologically compatible, water insoluble, and non-maleable polymer. Other polymers meeting one or more of the general requirements also be used. In certain embodiments, the splint is made of metal or wood.

When a splint having fins is used, the anterior surface of an upper fin, i.e., the mesial surface of a fin on the splint for the upper jaw, contacts the posterior surface of a lower fin, i.e., the distal surface of a fin on the splint for the lower jaw. In some embodiments, the surfaces make an angle of about 90° with the patient's occlusal plane, while in other embodiments, the angle is obtuse, and in still other embodiments, the angle is acute. In some embodiments, the angle is 90°, while in other embodiments, the angle is between about 20° to about 80°, for example, an angle selected from the group consisting of about 20°, about 25°, about 30°, about 35°, about 40°, about 45°, about 50°, about 55°, about 60°, about 65°, about 70°, about 75°, and about 80°. In other embodiments, the angle is between about 100° to about 160°, for example, an angle selected from the group consisting of about 100°, about 105°, about 110°, about 115°, about 120°, about 125°, about 130°, about 135°, about 140°, about 145°, about 150°, about 155°, and about 160°.

Each one of these designs has a set of unique advantages that the HCP might find beneficial for the patient. The skilled artisan is familiar with the advantages. Thus, in some embodiments, the fin or strap design option is selected from the group consisting of, a normal fin, an acute fin, an obtuse fin, and straps in compression or traction setting.

In some embodiments, the set of clinical options further comprise an option selected from the group consisting of an open anterior, an anterior discluder, a scalloped occlusal surface, a lingual opening, a compliance chip, an AM positioner, a tapered posterior, a tongue attractor, a bruxism package, lingualess, full lingual coverage, edentulous, posterior lingual, anterior lingual, anterior lingualess, and monoblock.

In some embodiments, the HCP chooses a device having an open anterior. These embodiments, typically direct the HCP to shy away from choosing an anterior hinge. Anterior discluders, such as the Best-Bite™ discluder (Whip Mix, Louisville, KY), are well known in the art. If the HCP chooses to incorporate an anterior discluder, it can be modeled into the splint design and manufactured as a monoblock along with the splint.

In a device with "scalloped occlusal surface" the occlusal surface of the splint, for example the molar area, is contoured to match the occlusal surface of the dentition.

Devices with a "lingual opening" or "anterior opening" are devices that have an opening in the anterior portion of the device that allows for air to move in and out of the mouth even when the mouth is partially closed.

Some insurance companies require patient's in certain professions, for example long haul truck drivers, to show that the device is being used in compliance with the HCP's instructions. Some devices comprise an electronic microchip that records the date and time the device was in use and the date and time the device was not in use. The data from these "compliance chips" can then be downloaded and communicated with the insurance company or another monitoring agency. In some embodiments, where such compliance chip is required or recommended, HCP chooses to include the chip in the splint design. The automated manufacturing machine is then programmed to include a space for the chip. The chip can then be inserted either automatedly or manually.

Following the overnight use of a mandibular advancement device, the joints and muscles of the jaw may experience fatigue, spasms, and pain because the mandible has been held in a forward, unnatural position for several hours. An AM positioner, or a morning positioner, for example Good Morning Positioner (Space Maintainers Laboratories, Chatsworth, CA) will assist to restore the jaw in the proper position. In some embodiments, the HCP chooses to provide additional instructions for the design of an AM positioner, in addition to the instructions for the splint design, or independent of the splint design, as the same patient data would be used in the manufacturing of both devices.

When a foreign device is inserted into the mouth, subconsciously the mouth continues to explore the new device, leading to tongue fatigue, which in turn leads to the tongue falling back in the mouth and further aggravating or producing a sleep apnea condition. In addition, tongue exploration of the device can lead to more anterior tongue activity and protrusions. An attractor can promote this even further to enhance tongue protrusion and increase muscle tone for a more viable airway. By strategically positioning a tongue attractor, e.g., a dent, a boss, a ridged or rough surface, and the like, in the splint, the tongue seeks the attractor and stays in position over the attractor, reducing or eliminating tongue fatigue, and/or enhanced tongue protrusion. In some embodiments, either the lower or upper, or both, splint has organic shapes as part of the design to increase the natural feel and comfort of the device, and to also activate the tongue via proprioceptive pathways, which cause the tongue and/or the muscle structure surrounding the airway respond to keep the airway open leading to a reduction in airway related symptoms. In some embodiments, the tongue attractor is one or more tori located in the anterior portion of the splint.

Individuals with bruxism, i.e., night-time teeth grinding, regularly are prescribed a bruxism package, which comprises a mouth guard that will protect the teeth during the subconscious grinding. In some embodiments, where the patient suffers from bruxism in addition to sleep apnea, the HCP chooses to include a bruxism package with the splint design. In some embodiments, the bruxism package is designed from the same set of patient data provided from the HCP.

In some embodiments, the selection of certain embodiments of an option renders the selection of certain embodiments of another option moot. For example, if the HCP chooses to select Microtitration Series for the titration mechanism, then the HCP will not be permitted to choose a Herbst hinge for the titration accessories. Instead, only accessories associated with the Microtitration Series, for example fixed or removable fins, will be available. The "smart" Rx allows only combinations of features such as the titration mechanism or any other features of the design that meet the clinical and engineering requirements of making a safe and useful device. Combinations for the selected features are presented visually to the HCP for verification of their selection.

Data Handling

Once all the selections are made on the website, the HCP communicates the selections with the MFG by any method currently known in the art, or later developed, for sending data through a web portal, for example, by clicking on a "SEND" icon at the bottom of the page, and the like. At this point, the HCP may also transmit the data regarding the patient's dentition impression to the laboratory as well. These data may include photographs, scanning data files, and the like. In some embodiments, the HCP transmits the two sets of the data (selections and impression) simultaneously. In other embodiments, the HCP transmits one set of data prior to the other set of data, for example, by transmitting each set of data shortly after it is obtained.

In some embodiments, the data is communicated electronically. In some of these embodiments, the HCP transmits the data files by electronic mail. In other embodiments, the HCP transmits the data files by uploading and transmitting the files through a website. In some embodiments the data is incorporated into a 3D PDF, such as that provided by Adobe® (https://helpx.adobe.com/acrobat/using/displaying-3d-models-pdfs.html).

In some embodiments, a first HCP obtains the impression data and a second, different, HCP prepares the selections. In some embodiments, the first and the second HCP are coworkers while in other embodiments, they are not coworkers. In some embodiments, the same HCP who obtains the impression data is the same individual as the HCP who prepares the selections.

As mentioned above, from the dentition impression data a design of the patient's dentition is obtained, for example using CAD, by methods well-known in the art. In other embodiments, the HCP prepares the design and transmits it to the MFG. In other embodiments, the MFG obtains the raw data from the HCP and prepares the design in-house.

In some embodiments, the HCP is in possession of all the patient data and design specifications used to treat the patient. The HCP can then draw conclusions and/or trends as to which design features are best suited for the treatment of which anomalies. In some embodiments, the data from all the HCPs is aggregated in one database to obtain a more accurate design-efficacy relationship for each patient anomaly. This process is sometimes referred to as "phenotyping," where a single or combination of design specifications is correlated with the treatment of a single malady. Whether aggregate data or single-HCP data us used, the result would be a more efficient treatment plan for future patients.

Subsequently, the computerized design of a dental device is prepared, taking into account the HCP's selections. The CAD file containing the design is then communicated to an automated manufacturing machine.

Manufacturing

The final stage of the process is the manufacture of the dental device. The CAD file containing the data related to the manufacture of the dental device is communicated with an automated manufacturing system.

In some embodiments, the appliance is manufactured additively, while in other embodiments, the appliance is manufactured subtractively. By "additive manufacturing" it is meant that the future device begins at a nucleus and grows from the nucleus. Examples of additive manufacturing include 3D printing (where the device grows out of a pool of monomers), injection molding (where the mold is filled with the monomer). By "subtractive manufacturing" it is meant that the future device is carved out of a block of material. Examples of subtractive manufacturing include hand carving and milling, e.g., an automated milling machine.

In some embodiments, depending on the type of selections made by the HCP, some clinical options, such as the Herbst lock or ball clasps, are incorporated into the device subsequent to the manufacturing step. In some embodiments, these clinical options are added automatedly by either the manufacturing device or another machine, while in other embodiments the clinical options are added manually. In some embodiments the device is the result of assembly of parts from both additive and subtractive manufacturing. The fully manufactured device is then provided to the patient either by the MFG or the HCP.

In some instances, the HCP may be unsure of what titration mechanism works best for the patient, or that the patient may benefit from different types of titration mechanisms as the treatment progresses. For example, the HCP may require a Herbst mechanism for the initial stages of the treatment, but would like to switch to a microtitration or a strap mechanism when the patient's mandibular position approaches the desired location or for maintenance therapy. In these embodiments, the splints are designed and manufactured with an attachment mechanism, such as a ball-clasp system, friction lock, a nut for a screw-on attachment, and the like. One example of the attachment mechanism is disclosed in the U.S. Pat. No. 9,615,964, incorporated by reference herein in its entirety including the drawings. The splints and the attachments are then manufactured separately. The HCP can then swap out the attached mechanism for a different one as the needs of the patient change.

In another aspect, disclosed herein is a dental device that is manufactured by the methods disclosed above.

In another aspect, disclosed herein is a method of treating or ameliorating a jaw-related disorder in a patient by obtaining a dental device manufactured by the methods disclosed above and positioning the dental device over the dentition prior to sleep. The device then advances the mandible forward relative to the maxilla, thereby ameliorating the symptoms of sleep apnea or the jaw-related disorder. In some embodiments, the method further comprises instructing the patient in the use of the device. In some embodiments, the jaw-related disorder is selected from temporomandibular disorder (TBD), poorly positioned temporomandibular joint (TMJ), or aesthetic deficiencies.

What is claimed is:

1. A method of manufacturing a set of mandibular advancement devices (MADs), the method comprising:
    a. obtaining a three-dimensional electronic model of a patient's dentition;
    b. converting, by a computer processor, the three-dimensional electronic model to a data set;
    c. obtaining, by the computer processor, clinical options data corresponding to a set of clinical options for treating the patient,
    d. incorporating, by the computer processor, within a computer-aided design data, the data set and the clinical options data, wherein the computer-aided design data corresponds to the set of MADs;
    e. automatedly manufacturing the set of MADs based on the computer-aided design data incorporating the clinical options data and the data set,
    wherein the set of MADs comprises at least one upper splint and at least one lower splint,
    wherein each of the at least one upper splint and each of the at least one lower splint comprise:
        an upper fin and a lower fin, respectively, or
        an upper post with the upper fin attached thereto and a lower post with the lower fin attached thereto, respectively,
    wherein the upper fin or the upper post is located at a distance UD from the back of the upper splint, and each lower fin or lower post is located at a distance LD from the back of the lower splint; and
    f. providing a set of sleeves,
    wherein each sleeve in the set of sleeves is configured fit into the lower fin, the lower post, the upper fin, or the upper post,
    wherein each sleeve in the set of sleeves comprises a shell having a wall defining a hollow interior and an opening at one end of the sleeve,
    wherein the hollow interior comprises approximately the size and dimensions corresponding to the lower fin, the lower post, the upper fin, or the upper post, wherein each sleeve in the set of sleeves has a different thickness from another sleeve in the set of sleeves with respect the wall and the shell,
    wherein the set of MADs comprises three or more splints with the at least one upper splint and the at least one lower splint.

2. The method of claim 1, wherein the three or more splints are designed digitally and manufactured according to a digital design.

3. The method of claim 1, wherein the upper fin comprises a front surface and a sleeve of the set of sleeves configured to fit into the lower post or the lower fin comprises a back surface, wherein, when both an upper splint of the at least one upper splint and a lower splint of the at least one lower splint are worn by a patient, with the sleeve fit into the lower post or the lower fin, the front surface of the upper fin contacts the back surface of the sleeve along a contact surface.

4. The method of claim 1, wherein a sleeve of the set of sleeves configured to fit into the upper post or the upper fin comprises a front surface and the lower fin comprises a back surface, wherein, when both an upper splint of the at least one upper splint and a lower splint of the at least one lower splints are worn by a patient, with the sleeve fit into the upper post or the upper fin, the front surface of the sleeve contacts the back surface of the lower fin along a contact surface.

5. The method of claim 1, wherein the shape of the upper fin or the lower fin is independently selected from a predesigned digital library.

6. The method of claim 1, wherein a sleeve of the set of sleeves comprises a locking mechanism.

7. The method of claim 6, wherein the locking mechanism is a friction lock mechanism or a key-tab mechanism.

8. The method of claim 1, wherein the set of clinical options comprises two or more clinical options selected from the group consisting of a titration mechanism, a titration accessory, a splint design, a retention mechanism, a splint material, and a fin or a strap design.

9. The method of claim 8, wherein the titration mechanism is selected from the group consisting of a microtitration series, a jack screw titration, a Herbst hinge titration, an anterior hinge titration, a strap titration, and a mechanical hook.

10. The method of claim 8, wherein the splint material is selected from the group consisting of standard polymethylmethacrylate (PMMA), lined PMMA, high-strength polyetheretherketone (PEEK), polymer produced from polyoxymethylene and acetal copolymers, glycol modified polyethylene terephthalate (PETg), and a physiologically compatible, water insoluble, non-maleable polymer.

11. The method of claim 1, wherein the distances UD and LD are independently unchangeable.

12. The method of claim 1, wherein
    a first sleeve and a second sleeve of the set of sleeves each connect by a locking mechanism to the upper fin, the lower fin, the upper post, or the lower post;
    wherein a thickness of the first sleeve is different than the thickness of the second sleeve;
    wherein, when the first sleeve or the second sleeve is connected by the locking mechanism to added to the upper fin, the lower fin, the upper post, or the lower post, the first sleeve or the second sleeve affords a rake angle of from about 20° to about 80°, from about 80° to about 100°, or from about 100° to about 160°.

13. The method of claim 1, further comprising adding or incorporating into each MAD of the set of MADs a Herbst lock or ball clasps subsequent to the manufacturing the set of MADs.

14. The method of claim 1, wherein the wall has a thickness in the range of from between about 1 µm to about 5 mm.

15. The method of claim 1, wherein the three-dimensional electronic model of the patient's dentition is obtained from direct scanning of the patient's dentition, and then importing data from the electronic scanning into a process processing the computer-aided design data.

16. The method of claim 1, wherein the set of clinical options is derived from a health care provider (HCP).

17. The method of claim 1, wherein the three-dimensional electronic model of the patient's dentition further comprises measuring a patient's natural arc of dentition, and the at least one upper splint and at least one lower splint contact each other in a patient's mouth along an engagement surface, and the engagement surfaces of the at least one upper splint and at least one lower splint are designed and manufactured to fit the natural arc of the patient's dentition.

18. The method of claim 14, wherein an image of the patient's dentition is made by taking a plaster model of a patient's dentition, and then electronically scanning the plaster model and importing data from the electronic scanning into a process processing the computer-aided design data.

19. The method of claim 1, wherein the set of sleeves provide for increments of advancement of a lower jaw for titrating prognathic movement of a mandible.

20. The method of claim 1, wherein the set of MADs further comprises a set of secondary sleeves, wherein each secondary sleeve of the set of secondary sleeves fits over a sleeve of the set of sleeves, and each secondary sleeve of the set of secondary sleeves has a different thickness than another secondary sleeve of the set of secondary sleeves.

21. The method of claim 20, wherein each sleeve of the set of sleeves has a different color than each sleeve of the set of secondary sleeves.

22. The method of claim 21, wherein each sleeve of the set of sleeves has a different color than each secondary sleeve of the set of secondary sleeves and when a secondary sleeve of the set of secondary sleeves fits over a sleeve of the set of sleeves a new color is formed.

* * * * *